United States Patent
Klimko et al.

(10) Patent No.: US 6,545,045 B1
(45) Date of Patent: Apr. 8, 2003

(54) PROSTAGLANDIN E AGONISTS FOR TREATMENT OF GLAUCOMA

(75) Inventors: Peter G. Klimko, Fort Worth, TX (US); Najam A. Sharif, Arlington, TX (US); Brenda W. Griffin, Cookeville, TN (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/485,217

(22) PCT Filed: Dec. 22, 1999

(86) PCT No.: PCT/US99/30746

§ 371 (c)(1),
(2), (4) Date: Feb. 4, 2000

(87) PCT Pub. No.: WO00/38667

PCT Pub. Date: Jul. 6, 2000

Related U.S. Application Data

(60) Provisional application No. 60/113,695, filed on Dec. 24, 1998, and provisional application No. 60/113,697, filed on Dec. 24, 1998.

(51) Int. Cl.[7] ............................................. A61K 31/215
(52) U.S. Cl. ..................... 514/530; 514/573; 514/913
(58) Field of Search ................................ 514/530, 573, 514/913

(56) References Cited

U.S. PATENT DOCUMENTS

| | | | |
|---|---|---|---|
| 4,822,819 | A | 4/1989 | DeSantis et al. |
| 4,952,581 | A | 8/1990 | Bito et al. |
| 5,057,621 | A | 10/1991 | Cooper et al. |
| 5,462,968 | A | 10/1995 | Woodward |
| 5,698,598 | A | 12/1997 | Woodward |
| 5,773,471 | A | 6/1998 | Oguchi et al. |
| 5,811,443 | A | 9/1998 | DeSantis et al. |

FOREIGN PATENT DOCUMENTS

| | | |
|---|---|---|
| EP | 561073 A1 | 9/1993 |
| EP | 603800 A1 | 6/1994 |

OTHER PUBLICATIONS

Alm, "Prostaglandin derivates as ocular hypotensive agents," *Progress in Retinal and Eye Research*, 17(2):291–312 (1998).

Anthony et al., "Prostaglandin $F_{2\alpha}$ receptors in the human trabecular meshwork, " *Invest. Ophthalmol. Vis. Sci.* , 39(2):315–321 (1998).

Bito, "Prostaglandins: a new approach to glaucoma management with a new, intriguing side effect, " *Survey of Ophthalmology* 41 (supplement 2) S1–S14 (1997).

Breyer et al., "Differential localization of prostaglandin E receptor subtypes in human kidney," *American J. Physiology* 270 (5 Pt 2): F912–F918 (1996).

Chomczynski and Sacchi, "Single–Step method of RNA isolation by acid guanidinium thiocyanate–phenol–chloroform extraction," *Analytical Biochemistry*, 162:156–159 (1987).

Clark et al., "Glucocorticoid–induced formation of cross–linked actin networks in cultured human trabecular meshwork cells, " *Investigative Ophthalmology & Visual Science*, 35(1):281–294 (1994).

Coleman et al., "A novel inhibitory prostanoid receptor in piglet saphenous vein, "*Prostaglandins*, 47: 151–167 (1994).

Crider et al, "Prostaglandin–stimulated adenylyl cyclase activity via a pharmacologically–defined $EP_2$ receptor in human non–pigmented cilliary epithelial cells, "*J. Ocular Pharmacology & Therapeutics*, 14(4):293–304 (1998).

Crider et al, "Use of semi–automated, robotic radioimmunoassay to measure cAMP generated by activation of DP–, $EP_2$– and IP–prostaglandin receptors in human ocular and other cell–types," *Prostaglandins, Leukotrienes & Fatty Acids*, 59(1):77–82 (1998).

de Brum–Fernandes et al., "Characterization of the $PGE_2$ receptor subtype in bovine chondrocytes in culture, " *British J. Pharmacology*, 118(7):1597–1604 (1996).

Flach et al., "Topical Prostaglandin $E_2$ Effects on Normal Human Intraocular Pressure," *Journal of Ocular Pharmacology*, 4(1):13–18 (1988).

Ichikawa, et al., "Molecular Aspects of the Structures and Functions of the Prostaglandin E Receptors," *J. Lipid Mediators Cell Signaling* 14:83–87 (1996).

Lutjen–Drescoll, "Functional morphology of the trabecular meshwork in primate eyes, "*Progress in Retinal and Eye Research*, 18(1):91–119 (1998).

Milne et al., "Human moncytes and cultured Chinese hamster ovary cells both express $EP_4$ receptors positively coupled to adenylate cyclase," *Br. J. Pharmacology*, 113 (supplement):8 (1994).

Morimoto et al., "Cellular localization of mRNAs for prostaglandin E receptor subtypes in mouse gastrointestinal tract" *American J. Physiology* 272 (3 Pt 1):G681–G687 (1997).

Mukhopadhyay et al., "Detection of $EP_2$, $EP_4$, and FP receptors in human ciliary epithelial and ciliary muscle cells, "*Biochemical Pharmacology*, 53(9):1249–1255 (1997).

Sakairi et al., "Luminal prostaglandin E receptors regulate salt and water transport in rabbit cortical collecting duct, "*American J. Physiology*, 269 (2 Pt 2):F257–F265 (1995).

(List continued on next page.)

*Primary Examiner*—Zohreh Fay
(74) *Attorney, Agent, or Firm*—Barry Copeland

(57) ABSTRACT

This application relates to compositions and methods for the treatment of glaucoma and/or ocular hypertension in mammals utilizing prostaglandin E receptor agonists.

2 Claims, No Drawings

OTHER PUBLICATIONS

Senchyna and Crankshaw, "Use of reverse transcription–polymerase reaction to identify prostanoid receptor mRNA in human myometrium, "*British J. Pharmacology*, 116:280 (1995).

Sharif et al., "Pharmacological analysis of mast cell mediator and neurotransmitter receptors coupled to adenylate cyclase and phospholipase C on immunocytochemically–defined human conjunctival epithelial cells," *J. Ocular Pharmacology & Therapeutics*, 13(4):321–336 (1997).

Waterbury, et al., "$EP_3$, But Not $EP_2$, FP, or TP Prostanoid–Receptor Stimulation May Reduce Intraocular Pressure," *Investigative Ophthalmology and Visual Science*, 31(12):2560–2567 (1990).

Weinreb et al., "Prostaglandins increase matrix metalloproteinase release from human ciliary smooth muscle cells," *Investigative Ophthalmology & Visual Science*, 38(13):2772–2780 (1997).

Woodward et al., "Intraocular Pressure Effects of Selective Prostanoid Receptor Agonists Involve Different Receptor Subtypes According to Radioligand Binding Studies," *J. of Lipid Mediators*, 6:545–553 (1993).

Woodward et al., "Molecular Characterization and Ocular Hypotensive Properties of the Prostanoid $EP_2$ Receptor," *Journal of Ocular Pharmacology and Therapeutics*, 11(3):447–454 (1995).

Andley et al., "The role of prostaglandins $E_2$ and $F_{2\alpha}$ in ultraviolet radiation–induced cortical cataracts in vivo" *Investigative Ophthalmology and Visual Science* 37(8):1539–1548 (1996) XP–000951411.

Crider et al., "Prostaglandin–stimulated adenylyl cyclase activity via a pharmacologically defined $EP_2$ receptor in human nonpigmented ciliary epithelial eells" *Journal Of Ocular Pharmacology and Therapeutics* 14(4):293–304 (1998) XP–000951407.

Shepard & Shrum, "Pars plana molteno implantation in complicated inflammatory glaucoma" *Ophthalmic Surgery* 26(3):218–222 (1995) XP–000951406.

Zahn et al., "Effect of prostaglandins on cyclic AMP production in cultured human ciliary muscle cells" *Journal of Ocular Pharmacology and Therapeutics* 14(1):45–55 (1998).

PROSTAGLANDIN E AGONISTS FOR TREATMENT OF GLAUCOMA

This application is a 371 of PCT/US99/30746 filed on Dec. 22, 1999, which claims benefit of provisional application Ser. Nos. 60/113,695 and 60/113,697 both filed Dec. 24, 1998.

FIELD OF THE INVENTION

The present invention relates to the use of certain analogs of E series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (EP 0 561 073 A1). Of interest in the present invention are compounds which are believed to exhibit IOP lowering mechanisms similar to those exhibited by $PGE_2$ (an E-series prostaglandin):

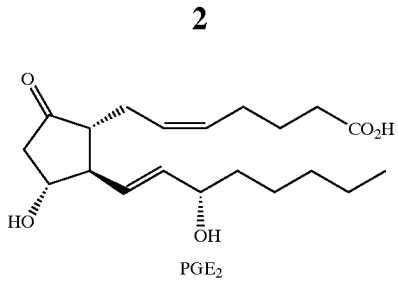

$PGE_2$

The relationship between EP receptor activation and IOP lowering effects is also not well understood. There are currently four recognized subtypes of the EP receptor ($EP_1$, $EP_2$, $EP_3$, and $EP_4$; *J. Lipid Mediators Cell Signaling*, volume 14, pages 83–87 (1996)). It is known in the art that ligands capable of $EP_2$ receptor activation, such as $PGE_2$ and synthetic analogs (*Journal of Ocular Pharmacology*, volume 4, number 1, pages 13–18 (1988); *Journal of Ocular Pharmacology and Therapeutics*, volume 11, number 3, pages 447–454 (1995); *Journal of Lipid Mediators*, volume 6, pages 545–53 (1993); Woodward, U.S. Pat. No. 5,698,598; Woodward, U.S. Pat. No. 5,462,968), or $EP_3$ receptor activation (*Journal of Lipid Mediators*, volume 7, pages 545–553 (1993); *Investigative Ophthalmology and Visual Science*, volume 31, number 12, pages 2560–2567 (1990)) lower IOP. However, some of these molecules have also been associated with undesirable side effects resulting from topical ophthalmic dosing, including an initial increase in IOP, photophobia, and eye ache (see for example *Journal of Ocular Pharmacology*, volume 4, number 1, pages 13–18 (1988)).

Based on the foregoing, a need exists for the development of molecules that may activate the PGE receptors, yielding a more efficacious lowering of IOP, while exhibiting fewer or reduced side effects.

An agent which exhibits comparable or improved efficacy, but with reduced side effects when compared to other agents, is said to have an improved therapeutic profile. It is an object of this invention to provide a class of IOP lowering agents with an improved therapeutic profile over $PGE_2$, and methods of their use. It has now unexpectedly been discovered that the presently claimed prostanoids meet this objective. Although certain analogs of prostaglandin $E_2$ have been disclosed as ocular hypotensives in U.S. Pat. Nos. 5,057,621; 5,698,598; 5,462,968; and 4,822,891, and by Woodward el al., *J. Lipid Mediators*, 6:545 (1993), the presently claimed compounds of this invention are neither disclosed, claimed, nor suggested in that art. Furthermore, certain compounds of the claimed invention in combination with prostaglandin FP receptor agonists (EP 603800 A1) or with clonidine derivatives (U.S. Pat. No. 5,811,443) have been claimed for treating glaucoma.

SUMMARY OF THE INVENTION

The present invention is directed to novel compositions, and methods of use in treating ocular disorders in mammals, and especially in humans. More specifically, and in preferred embodiments, the present invention encompasses compositions containing certain prostaglandin E receptor agonists and methods for treating glaucoma and ocular hypertension.

DETAILED DESCRIPTION OF THE INVENTION

It has unexpectedly been found that the prostaglandin E agonists of the present invention exhibit an improved therapeutic profile in the treatment of glaucoma and ocular hypertension when compared to natural prostaglandins and many of their known analogs. The prostaglandin E agonists of the present invention may also be used to treat other ocular disorders, such as optic nerve disorder, by retarding visual field loss and/or improving visual acuity in the manner described in U.S. Pat. No. 5,773,471, the disclosure of which is incorporated herein by this reference. As used herein, the terms "treat," "treating," and "treatment" include both active treatment of the targeted disorder or symptoms thereof, as well as prophylactic treatment of those disorders or symptoms in susceptible or at risk patients. It is further intended and should be understood that treatment of disorders stated in the conjunctive, such as "glaucoma and ocular hypertension," includes the disjunctive as well. The phrase should therefore be read to mean "glaucoma and/or ocular hypertension."

It is further contemplated that the compounds of the present inventions can be used with other medicaments known to be useful in the treatment of glaucoma or ocular hypertension, either separately or in combination. For example, the prostaglandin E agonists of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811.443); and (iv) cholinergic agonists, such as pilocarpine. The disclosures of U.S. Pat. Nos. 4,952,581 and 5,811,443 are incorporated herein by this reference. Specifically included in such definition are compounds of the following formula I:

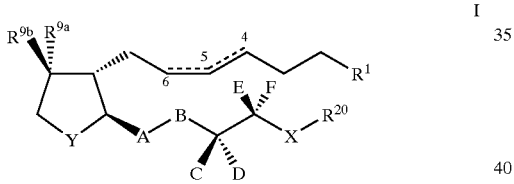

I wherein:
$R^1$=$(CH_2)_nCO_2R$, $(CH_2)_nCONR^4R^5$, $(CH_2)_nCH_2OR^6$, $(CH_2)_nCH_2NR^7R^8$, where:
R=H or pharmaceutically acceptable cationic salt moiety, or $CO_2R$ forms a pharmaceutically acceptable ester moiety;
$R^4$, $R^5$=same or different=H, alkyl, or $SO_2CH_3$, with the proviso that if one of $R^4$, $R^5$=$SO_2CH_3$, then the other=H or alkyl;
$R^6$=H, acyl, or alkyl;
$R^7$, $R^8$=same or different=H, acyl, or alkyl; with the proviso that if one of $R^7$, $R^8$=acyl, then the other=H or alkyl,
n=0 or 2;
---=single or double bond, which can be cumulated (i.e., carbons 4–6 can form an allene);
$R^{9b}$=Cl, and $R^{9a}$=H, or $R^{9b}R^{9a}$ taken together=O as a carbonyl;
Y=$CH_2$, O, or

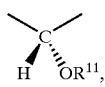

where $R^{11}$=H, alkyl, or acyl;

A=O and B=$CH_2$; or, A—B=$CH_2CH_2$ or cis-CH=CH; with the proviso that A≠O when Y=O;
one of C, D=H, and the other=$CH_3$ or $OR^2$, where $R^2$=H, acyl, or alkyl or C=D=H;
E and F=same or different=H or $CH_3$; or one of E, F=$CH_3$ and the other=$OR^2$, where $R^2$ is defined as above; with the proviso that exactly one of C, D, E, and F=$OR^2$;
X=O or direct bond;
$R^{20}$=$C_{2-8}$ alkyl $C_{2-8}$ alkenyl, aryl, heteroaryl, aryloxy, or heteroaryloxy, optionally substituted with halo, trihalomethyl, $OR^3$, $NR^3R^{21}$, wherein $R^3$=H, alkyl, or acyl; and
$R^{21}$=H, alkyl, or acyl; with the proviso that if one of $R^3$ and $R^{21}$=acyl, then the other=H or alkyl; and wherein the $C_{2-8}$ alkyl and $C_{2-8}$ alkenyl may be optionally terminated by $C_{3-8}$ cycloalkyl, $C_{4-8}$ cycloalkenyl, aryl, heteroaryl, aryloxy, or heteroaryloxy, optionally substituted as described above; with the proviso that $R^{20}$≠aryloxy or heteroaryloxy when X=O;

with the proviso that all of the following compounds be excluded:
compounds of formula II:

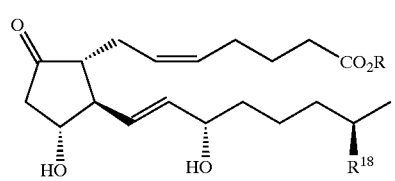

II wherein:
$CO_2R$ is as defined above; and
$R^{18}$ is H or OH;
compounds of formula III:

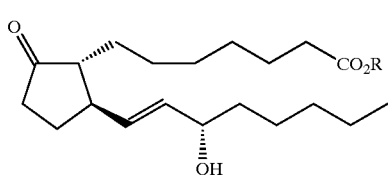

III wherein:
$CO_2R$ is as defined above;
and compounds 1 and 2:

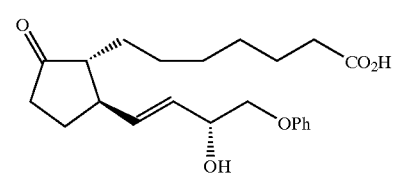

1

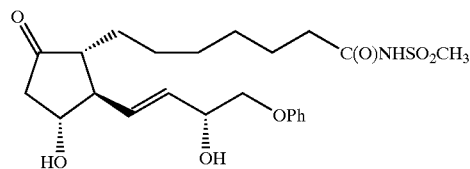

2

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.: Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation. nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, the terms "pharmaceutically acceptable ester"/"pharmaceutically acceptable cationic salt" means any ester/cationic salt that would be suitable for therapeutic administration to a patient by any conventional means without significant deleterious health consequences; and "ophthalmically acceptable ester"/"ophthalmically acceptable cationic salt" means any pharmaceutically acceptable ester/cationic salt that would be suitable for ophthalmic application, i.e. non-toxic and non-irritating. Wavy line attachments indicate that the configuration may be either alpha (α) or beta (β). The carbon numbering is as indicated in formula I, even when n=2. Dashed lines on bonds [e.g., between carbons 4 (C-4) and 5 (C-5] indicate a single or double bond. The presence of two solid lines specifies the configuration of the relevant double bond. Hatched lines indicate the α configuration. A solid triangular line indicates the β configuration.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl. alkoxy, or lower alkyl. Preferred cycloalkyl groups include cyclopropyl, cyclobutyl, cyclopentyl and cyclohexyl.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "alkoxy" represents an alkyl group attached through an oxygen linkage.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

One preferred class of compounds for purposes of the present invention are those compounds which exhibit $EP_4$ receptor binding activity, hereinafter $EP_4$ receptor binding agents ("RBAs"). The $EP_4$ prostaglandin receptor belongs to a family of prostaglandin receptors, all of which have seven-transmembrane domains and couple to specific G-proteins. When the $EP_4$ receptor on the cell surface is activated by the binding of a specific agonist ligand (a prostaglandin belonging to one of several defined classes of prostaglandins) the conformation of the G-protein is modified to favor the coupling to the enzyme adenylate cyclase (inside the cell). This event then leads to the hydrolysis of ATP to generate the intracellular second messenger cyclic AMP (cAMP) (Coleman et al., VIII International Union of Pharmacology classification of prostanoid receptors: Properties, distribution, and structure of the receptors and their subtypes, *Pharmacological Reviews*, 45:205–229 (1994)). The cAMP produced in this manner then leads to the activation of various cAMP-dependent enzymes which produce various biochemical events leading to the final biological response which may involve tissue contraction, hormone release or fluid and/or electrolyte secretion amongst other responses.

The $EP_4$ receptor is reported to be present in human ciliary epithelial cells and human ciliary muscle (CM) cells (Mukhopadhyay et al., Detection of $EP_2$, $EP_4$, and FP receptors in human ciliary epithelial and ciliary muscle cells. *Biochemical Pharmacology*, 53:1249–1255 (1997)). These ocular tissues are known to be heavily involved in the production of the aqueous humor. $EP_4$ receptors also modulate salt and water transport in the kidney (Sakairi et al. Luminal prostaglandin E receptors regulate salt and water transport in rabbit cortical collecting duct. *American J. Physiology*, 269 (2 Pt 2): F257–F265 (1995); Breyer et al. Differential localization of prostaglandin E receptor subtypes in human kidney. *American J. Physiology* 270 (5 Pt 2): F912–F918 (1996) and at many loci in the gastrointestinal tract (Morimoto et al. Cellular localization of mRNAs for prostaglandin E receptor subtypes in mouse gastrointestinal tract. *American J. Physiology* 272 (3 Pt 1): G681–G687 (1997)). $EP_4$ receptors can mediate the release of matrix metalloproteases which degrade extracellular matrix debris (de Brum-Fernandes et al. Characterization of the PGE2 receptor subtype in bovine chondrocytes in culture, *British J. Pharmacology* 118:1597–1604 (1996)). FP-class prostaglandins have also been reported to effect such mediation (Weinreb et al., Prostaglandins increase matrix metalloproteinase release from human ciliary smooth muscle cells. *Investigative Ophthalmology & Visual Science* 38:2770–2772 (1997)), and it has been suggested that such mediation by FP prostaglandins may be associated with IOP lowering. However, FP agonists may also directly lower IOP by activating FP receptors on trabecular meshwork cells (Anthony et al., Prostaglandin $F_{2\alpha}$ receptors in the human trabecular meshwork," Invest. Ophthalmol. Vis. Sci,. 39:315–321 (1998)). While certain DP-, $EP_2$- and FP-class prostaglandins lower IOP in animals and humans (Alm, Prostaglandin derivates as ocular hypotensive agents, *Progress in Retinal and Eye Research*, 17, 291–312 (1998); Bito, Prostaglandins: a new approach to glaucoma management with a new, intriguing side effect, *Survey of Ophthalmology*, 41 (supplement 2) S1–S14 (1997)), selective agonists for their respective receptors do not significantly activate the $EP_4$ receptor as shown in Table 1 below.

We have now discovered that $EP_4$ receptor mRNA is present in human trabecular meshwork cells (see example 2 below). Based on this unexpected discovery we theorize that potent and/or selective activation of the trabecular meshwork $EP_4$ receptors might yield a more efficacious lowering of IOP, while exhibiting fewer or reduced side effects when compared to conventional therapies.

Preferred for purposes of the present invention are those compounds of formula I wherein:

$R^1=(CH_2)_nCO_2R$ or $(CH_2)_nCH_2OR^6$; where: n=0; R=H, ophthalmically acceptable cationic salt moiety, or lower alkyl; and $R^6=H$;

---=single or double bond, which can be cumulated (i.e., carbons 4–6 can form an allene);

$R^{9b}=Cl$ and $R^{9a}=H$, or $R^{9b}R^{9a}=O$ as a carbonyl;

Y = 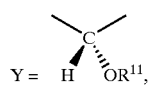, where $R^{11}=H$;
A—B=cis-CH=CH;
C=D=H;
one of E, F=$CH_3$ and the other=$OR^2$, where $R^2=H$;
X=direct bond: and $R^{20}=C_{2-5}$ alkyl or $C_{2-5}$ alkenyl optionally terminated by $C_{5-6}$ cycloalkyl or $C_{5-6}$ cycloalkenyl.

Also preferred for purposes of the present invention are those compounds of formula I, wherein:

$R^1=(CH_2)_nCO_2R$ or $(CH_2)_nCH_2OR^6$; where: n=0; R=H, ophthalmically acceptable cationic salt moiety, or lower alkyl; and $R^6=H$;

---=single or double bond, which can cumulated (i.e., carbons 4–6 can form an allene);

$R^{9b}=Cl$ and $R^{9a}=H$, or $R^{9b}R^{9a}=O$ as a carbonyl;

Y = 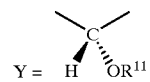

or $CH_2$ where $R^{11}=H$;
A—B=cis-CH=CH;
one of C=D=H, and the other=OH;
E=F=$CH_3$;
X=direct bond; and
$R^{20}=C_{2-5}$ alkyl or $C_{2-5}$ alkenyl optionally terminated by $C_{5-6}$ cycloalkyl or $C_{5-6}$ cycloalkenyl.

Also preferred for purposes of the present invention are those compounds of formula I, wherein:

$R^1=(CH_2)_nCO_2R$ or $(CH_2)_nCH_2OR^6$; where: n=0; R=H, ophthalmically acceptable cationic salt moiety, or lower alkyl; and $R^6=H$;

---=a double bond between carbons 4 and 5 and a single or double bond between carbons 5 and 6;

$R^{9a}R^{9b}=O$ as a carbonyl;

Y = 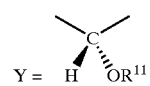

or $CH_2$, where $R^{11}=H$;
A—B=cis-CH=CH;
one of C=D=H, and the other=OH;
E=F=H;
X=O; and
$R^{20}=$phenyl, optionally substituted with Cl or $CF_3$.

Among the especially preferred compounds of the present invention are 11-deoxy-16,16-dimethyl $PGE_2$ and 16,16-dimethyl $PGE_2$, both of which are commercially available from Cayman Chemical Company, Ann Arbor, Mich., as well as the following compounds:

| Compound Name | Compound Structure | Synthesis Reference |
|---|---|---|
| enprostil | 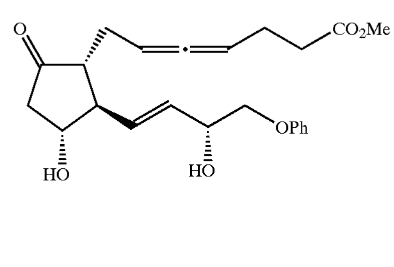 | Cooper et al., J. Org. Chem., 58: 4280–4286 (1993); Park et al., U.S. Pat. No. 5,571,936. |

-continued

| Compound Name | Compound Structure | Synthesis Reference |
|---|---|---|
| riprostil | 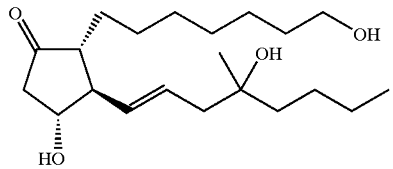 | Shriver et al., EP 66475 A2; Kluender et al., U.S. Pat. No. 4,132,738 |
| SC-46275 | 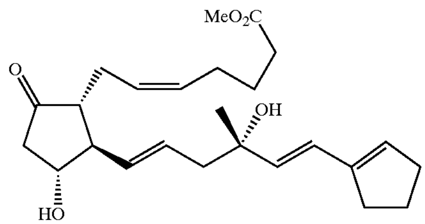 | Kalish et al., Synth. Commun., 20: 1641–5 (1990); Collins et al., J. Med. Chem., 33: 2784–93 (1990); Babiak et al., U.S. Pat. No. 5,055,604. |
| enisoprost | 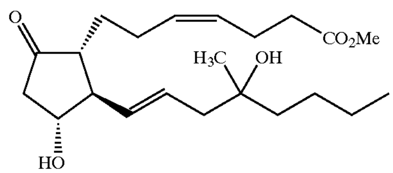 | Babiak et al., U.S. Pat. No. 5,055,604; Dygos et al., J. Org. Chem., 56: 2549–52 (1990). |
| nocloprost | 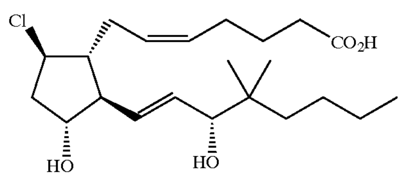 | Skuballa et al., U.S. Pat. No. 4,444,788. |
| misoprostol | 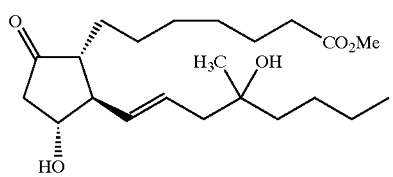 | Commercially available from Cayman Chemical Co., Ann Arbor, MI |

EXAMPLE 1

Immortalized human non-pigmented ciliary epithelial cells (containing $EP_2$ receptors) and Chinese hamster ovary cells (containing $EP_4$ receptors, Milne et al. Human moncytes and cultured Chinese hamster ovary cells express $EP_4$ receptors positively coupled to adenylate cyclase, *Br. J. Pharmacology*, 113 (supplement):8 (1994)) were stimulated with various prostaglandins for 15–60 min at 23° C. The cAMP produced by receptor activation was determined by a specific radioimmunoassay as previously described (Sharif et al., Pharmacological analysis of mast cell mediator and neurotransmitter receptors coupled to adenylate cyclase and phospholipase C on immunocytochemically-defined human conjunctival epithelial cells, *J. Ocular Pharmacology & Therapeutics*, 13, 321–336 (1997); Crider et al. Prostaglandin-stimulated adenylyl cyclase activity via a pharmacologically-defined $EP_2$ receptor in human non-pigmented epithelial cells, *J. Ocular Pharmacology & Therapeutics* 14:293–304 (1998); Crider et al. Use of a semi-automated, robotic radioimmunoassay to measure cAMP generated by activation of DP-, $EP_2$- and IP-prostaglandin receptors in human ocular and other cell-types, *Prostaglandins, Leukotrienes & Fatty Acids* 59:77–82 (1998), Milne et al. Human moncytes and cultured Chinese hamster ovary cells express $EP_4$ receptors positively coupled to adenylate cyclase, *Br. J. Pharmacology*, 113 (supplement) :8, (1994)). The dose-response curves for the prostaglandins were analyzed with an iterative, non-linear curve-fitting computer program to generate the relative potencies ($EC_{50}$= concentration of the compound which produces 50% of the maximal response) of the compounds. The smaller the $EC_{50}$ value the more potent the compound. Thus, as can be seen in Table 1 below, certain compounds were significantly more potent agonists at the $EP_4$ receptor than at the $EP_2$ receptor, making them relatively "$EP_4$-selective". On the other hand, butaprost and ZK118182 were more $EP_2$-selective compounds, whilst cloprostenol and fluprostenol ($EP_3$-/FP-selective) were inactive at the $EP_2$ and $EP_4$ receptors.

TABLE 1

Potency and Efficacy of Selected Prostaglandins at the
$EP_2$ and $EP_4$ Receptor Subtypes.

| Prostaglandins and Preferred Receptor Activation | Potency ($EC_{50}$, nM) at $EP_2$ Receptors in Immortalized Human Non-pigmented Ciliary Epithelial Cells | Potency ($EC_{50}$, nM) at $EP_4$ Receptors in Chinese Hamster Ovary Cells |
|---|---|---|
| $PGE_2$ (non-selective) | 38 nM (100% efficacy) | 35 nM (100% efficacy) |
| 11-deoxy-$PGE_1$ | 500 nM (100% efficacy) | 38 nM (86% efficacy) |
| 16,16-dimethyl-$PGE_2$ | 686 nM (97% efficacy) | 31 nM (100% efficacy) |
| 11-deoxy-16, 16-dimethyl-$PGE_2$ | 739 nM (75% efficacy) | 176 nM (99% efficacy) |
| ZK118182 (DP-selective agonist) | 700 nM (44% efficacy) | >10,000 nM |
| Butaprost ($EP_2$-selective agonist) | 212 nM (55% efficacy) | >10,000 nM |
| Fluprostenol (FP-selective agonist) | Inactive | Inactive |
| Cloprostenol (FP/$EP_3$-selective agonist) | Inactive | Inactive |

EXAMPLE 2

Total ribonucleic acid (RNA) was isolated from cells of interest using the well known guanidine thiocyanate-phenol-chloroform extraction procedure (Chomczynski and Sacchi, *Analytical Biochemistry*, 162: 156–163 (1987)). The isolated RNA was reverse transcribed into complementary DNA (cDNA) using the well known protocol outlined in the GeneAmp RNA PCR kit (Perkin Elmer/Cetus, Norwalk, Conn.). The technique of reverse transcriptase polymerase chain reaction (RT-PCR) using oligonucleotide primers for the different human prostaglandin receptors was employed to detect the messenger RNAs (mRNAs) for various prostaglandin receptors in human trabecular meshwork, choroidal and iridial melanocytes as previously described (Senchyna and Crankshaw, Use of reverse transcription-polymerase chain reaction to identify prostanoid receptor mRNA in human myometrium. *British J. Pharmacology*, 116: 280 (1995)). As can be seen in Table 2 below, whilst human trabecular meshwork cells expressed the $EP_4$ receptor mRNA in 3/3 experiments, neither the human choroidal nor the human iridial ocular melanocytes (serving as negative controls for human ocular cells) expressed the $EP_4$ receptor mRNA. Since the trabecular meshwork cells are heavily involved in IOP regulation (Clark et al. Glucocorticoid-induced formation of cross-linked actin networks in cultured human trabecular meshwork cells. *Investigative Ophthalmology & Visual Science*, 35: 281–294 (1994); Lutjen-Drescoll, Functional morphology of the trabecular meshwork in primate eyes. *Progress in Retinal and Eye Research*, 18, 91–119 (1998)), the presence of $EP_4$ receptors here suggests that $EP_4$ agonists and partial agonists would be expected to relax this tissue, as has been shown for other tissues (Coleman et al., A novel inhibitory prostanoid receptor in piglet saphenous vein. *Prostaglandins*, 47: 151–168 (1994)), which would result in lowering of IOP.

TABLE 2

RT-PCR data demonstrating the presence of $EP_4$ receptor mRNAs in the human ocular cells

| Cell Type | Detection of $EP_4$ Receptor mRNA (number of times $EP_4$ mRNA successfully detected in cell lysates from 2–3 experiments) |
|---|---|
| Human trabecular meshwork cells | 3/3 |
| Human choroidal melanocytes (line A08) | 0/2 |
| Human iridial melanocytes (line A47) | 0/2 |

The prostaglandin E agonists of the present invention may be contained in various types of pharmaceutical compositions, in accordance with formulation techniques known to those skilled in the art. In general, these compounds will be formulated in solutions for topical ophthalmic administration. Solutions, suspensions and other dosage forms are particularly preferred for the treatment of glaucoma and/or ocular hypertension.

The ophthalmic compositions of the present invention will include one or more compounds of the present invention in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the compounds of the present invention may also be readily incorporated into other types of compositions, such as suspensions, viscous or semi-viscous gels, or other types of solid or semi-solid compositions. Suspensions may be preferred for those compounds of the present invention which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the $EP_4$ agonists from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to decrease intraocular pressure and thus treat or improve glaucomatous conditions. As used herein, the term "pharmaceutically effective amount" refers to an amount which lowers intraocular pressure and/or improves the glaucomatous condition in a mammalian, preferably human, patient. When the compositions are dosed topically, they will gen erally be in a concentration range of from 0.001 to about 1.0% w/v, with 1–2 drops administered 1–4 times per day.

As used herein, the term "pharmaceutically acceptable carrier" refers to any vehicle which, when formulated, is safe, and provides the appropriate delivery for the desired route of administration of an effective amount of at least one prostaglandin E agonist of the present invention.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for the treatment of glaucoma and ocular hypertension in mammals, wherein such treatment is characterized by an improved therapeutic profile over that of $PGE_2$, comprising administering to an effected eye, a composition consisting essentially of a compound selected from the group consisting of: rioprostil, SC 46275, enisoprost, misoprostol, nocloprost, enprostil, 11-deoxy-16-16-dimethyl-$PGE_2$, and 16,16-dimethyl-$PGE_2$, and pharmaceutically acceptable esters and cationic salts thereof; in an amount sufficient to lower intraocular pressure.

2. The method of claim 1 wherein the compound is 11-deoxy-16,16-dimethyl-$PGE_2$, and its pharmaceutically acceptable esters and cationic salts.

* * * * *